(12) United States Patent
Gregg

(10) Patent No.: US 9,636,167 B2
(45) Date of Patent: May 2, 2017

(54) SURGICAL DEVICE WITH DC POWER CONNECTION

(75) Inventor: William N. Gregg, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 1233 days.

(21) Appl. No.: 13/149,570

(22) Filed: May 31, 2011

(65) Prior Publication Data

US 2012/0310229 A1    Dec. 6, 2012

(51) Int. Cl.
  *A61B 17/29*  (2006.01)
  *A61B 18/14*  (2006.01)
  *A61B 17/32*  (2006.01)
  *A61B 17/00*  (2006.01)
  *A61B 18/00*  (2006.01)
  *A61B 18/12*  (2006.01)

(52) U.S. Cl.
  CPC .. *A61B 18/1445* (2013.01); *A61B 17/320092* (2013.01); *A61B 18/1402* (2013.01); *A61B 2017/00734* (2013.01); *A61B 2018/00916* (2013.01); *A61B 2018/1226* (2013.01)

(58) Field of Classification Search
  CPC ................ A61B 17/320092; A61B 17/320068
  USPC ..................................................... 606/32–50
  See application file for complete search history.

(56) References Cited

U.S. PATENT DOCUMENTS

| | | | |
|---|---|---|---|
| 4,878,493 A * | 11/1989 | Pasternak et al. ............. | 607/99 |
| 5,697,808 A * | 12/1997 | Chen .................. | H04M 1/0262 |
| | | | 429/121 |
| 5,792,138 A * | 8/1998 | Shipp .............................. | 606/38 |
| 5,886,883 A | 3/1999 | Rail | |
| 5,935,143 A | 8/1999 | Hood | |
| 6,017,354 A | 1/2000 | Culp et al. | |
| 6,039,734 A * | 3/2000 | Goble ............................. | 606/41 |
| 6,056,735 A | 5/2000 | Okada et al. | |
| 6,090,123 A | 7/2000 | Culp et al. | |
| 6,108,227 A | 8/2000 | Voelkel | |
| 6,146,657 A | 11/2000 | Unger et al. | |
| 6,160,376 A | 12/2000 | Kumar et al. | |
| 6,235,027 B1 * | 5/2001 | Herzon .......................... | 606/51 |
| 6,293,946 B1 | 9/2001 | Thorne | |
| 6,331,761 B1 | 12/2001 | Kumar et al. | |
| 6,340,352 B1 | 1/2002 | Okada et al. | |
| 6,669,690 B1 | 12/2003 | Okada et al. | |

(Continued)

OTHER PUBLICATIONS

Extended European Search Report from EP Application No. 12793258.0 mailed Oct. 17, 2014.

(Continued)

*Primary Examiner* — Michael Peffley

(57) ABSTRACT

A system and method for providing additional power to a hand-held surgical device from a supplemental DC power supply. The hand-held surgical device includes a generator and an internal power supply. The internal power supply is a battery or a capacitor either which can withstand a high-temperature and/or a low-temperature sterilization procedure while within the hand-held surgical device. The supplemental DC power supply can provide alone or in combination with the internal power supply sufficient power to the generator to perform an electrosurgical procedure. The supplemental DC power supply is connected through a detachable cord to the hand-held surgical device. The DC power supply may be outside a sterile surgical environment.

17 Claims, 10 Drawing Sheets

(56) References Cited

U.S. PATENT DOCUMENTS

| | | |
|---|---|---|
| 7,092,265 B2 | 8/2006 | Kernahan |
| 7,517,351 B2 | 4/2009 | Culp et al. |
| 8,241,235 B2 * | 8/2012 | Kahler et al. .................. 602/34 |
| 8,690,866 B2 * | 4/2014 | Brannan ......................... 606/28 |
| 2002/0067080 A1 * | 6/2002 | Neumann ..................... 307/150 |
| 2004/0030328 A1 | 2/2004 | Eggers et al. |
| 2007/0035203 A1 | 2/2007 | Bromfield |
| 2008/0015566 A1 | 1/2008 | Livneh |
| 2008/0147058 A1 | 6/2008 | Horrell et al. |
| 2009/0142804 A1 | 6/2009 | Lee et al. |
| 2009/0143797 A1 * | 6/2009 | Smith et al. .................. 606/169 |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143805 A1 * | 6/2009 | Palmer ............. A61B 17/32009<br>606/169 |
| 2009/0157071 A1 | 6/2009 | Wham et al. |
| 2009/0209979 A1 * | 8/2009 | Yates ............... A61B 17/07207<br>606/143 |
| 2009/0248007 A1 | 10/2009 | Falkenstein et al. |
| 2010/0000074 A1 | 1/2010 | Smith et al. |
| 2010/0063494 A1 | 3/2010 | Orszulak |
| 2011/0118722 A1 * | 5/2011 | Lischinsky et al. ............ 606/33 |
| 2012/0059286 A1 * | 3/2012 | Hastings et al. .................. 601/2 |
| 2012/0116265 A1 * | 5/2012 | Houser ............ A61B 17/00234<br>601/2 |
| 2012/0116266 A1 * | 5/2012 | Houser et al. .................... 601/2 |

OTHER PUBLICATIONS

International Search Report from PCT/US2012/039837 mailed Oct. 24, 2012.

European Search Report from EP Application No. 12793258.0 mailed Nov. 19, 2015.

European Search Report EP12 793 258.0 dated Sep. 6, 2016.

* cited by examiner

SURGICAL DEVICE WITH DC POWER CONNECTION

BACKGROUND

1. Technical Field

The present disclosure relates to apparatuses and method for supplying power to a handheld surgical device, and more particularly, to a supplementary DC power source to increase the power supplied to a generator within the handheld surgical device.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high frequency electrical current to a surgical site to cut, ablate, coagulate or seal tissue. In monopolar electrosurgery, as shown in FIG. 1A, a source or active electrode 2 delivers high frequency energy from the electrosurgical generator 20 to the tissue and a return electrode 2 carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, as shown in FIG. 1B, one of the electrodes of the hand-held instrument functions as the active electrode 14 and the other as the return electrode 16. The return electrode is placed in close proximity to the active electrode such that an electrical circuit is formed between the two electrodes (e.g., electrosurgical forceps 10). In this manner, the applied electrical current is limited to the body tissue positioned immediately adjacent to the electrodes. When the electrodes are sufficiently separated from one another, the electrical circuit is open and thus inadvertent contact with body tissue with either of the separated electrodes does not cause current to flow.

Electrosurgical instruments have become widely used by surgeons in recent years. By and large, most electrosurgical instruments are hand-held instruments, e.g., an electrosurgical pencil, which transfer electrical or electrosurgical energy to a tissue site. As used herein the term "electrosurgical pencil" is intended to include instruments which have a handpiece that is attached to an active electrode and which is used to cauterize, coagulate and/or cut tissue. Typically, the electrosurgical pencil may be operated by a handswitch or a foot switch. The active electrode is an electrically conducting element that is usually elongated and may be in the form of a thin flat blade with a pointed or rounded distal end. Alternatively, the active electrode may include an elongated narrow cylindrical needle that is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material.

Some electrosurgical procedures utilize electrosurgical forceps that use both mechanical clamping action and electrical energy to affect hemostasis by heating tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are typically inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas. Such endoscopic instruments may use monopolar forceps, bipolar forceps or a combination monopolar/bipolar forceps.

Some portable battery powered surgical devices are powered by lithium-ion batteries. As these batteries require charging before use, a lithium-ion battery requires removal of the battery and sterilization in a hydrogen-peroxide system due to the low heat tolerance of lithium-ion batteries. Hydrogen-peroxide sterilization systems cost more money then high-temperature sterilization techniques and are not as widely available in all locations.

SUMMARY

In accordance with the present disclosure, a system and method for providing additional power to a hand-held surgical device from a supplemental DC power supply. The hand-held surgical device includes a generator and an internal power supply. The internal power supply is a battery or a capacitor either which can withstand a high-temperature or low temperature sterilization procedure while within the hand-held surgical device. The supplemental DC power supply can provide alone or in combination with the internal power supply sufficient power to the generator to perform an electrosurgical procedure. The supplemental DC power supply is connected through a detachable cord to the hand-held surgical device. The DC power supply may be outside a sterile surgical environment.

According to an embodiment of the present disclosure, an apparatus for performing a surgical procedure. The apparatus includes a hand-held surgical device having a generator and an internal power supply. The entire hand-held surgical device can withstand at least one type of high-temperature sterilization. The apparatus further includes a supplemental DC power supply in external communication with the internal power supply and a cord that connects the supplemental DC power supply to the hand-held internal power supply to increase the power supplied to the generator.

According to another embodiment of the present disclosure, an apparatus for performing a surgical procedure. The apparatus includes a hand-held surgical device having a generator and an internal battery. The internal battery while within the hand-held surgical device can withstand at least one type of high-temperature sterilization. The apparatus further includes a supplemental DC power supply in external communication with the internal battery and a cord that connects the supplemental DC power supply to the internal battery to increase the power supplied to the generator.

According to another embodiment of the present disclosure, a method for performing a surgical procedure includes the step of connecting a hand-held surgical device to a supplemental DC power supply. The hand-held surgical device includes an internal power supply and a generator within. The method further includes the steps of performing a surgical procedure and selectively augmenting power supplied to the generator via the internal power supply using the supplemental DC power supply. Alternatively, the supplemental DC power supply can directly supply power to the generator and the internal power supply can selectively augment power supplied to the generator, such as during peak usage requirements. The method also includes the steps of disconnecting the hand-held surgical device from the supplemental DC power supply and performing a high-temperature sterilization procedure on the hand-held surgical device including the internal power supply.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
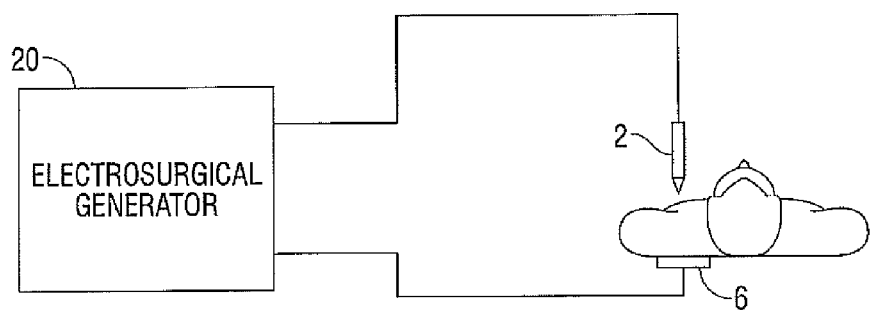
FIGS. 1A-1B are schematic diagrams of electrosurgical systems.
Figure 1B:
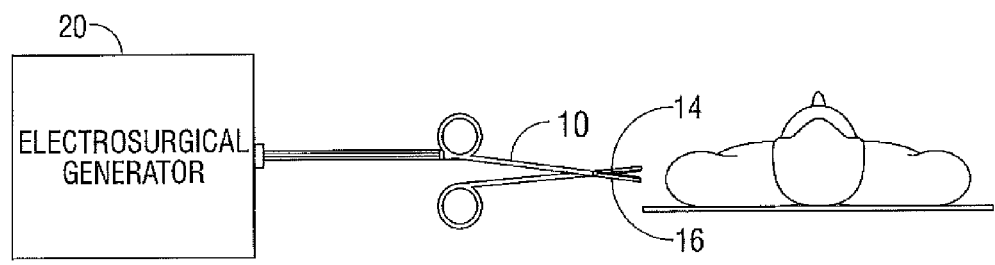

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves. Ultrasonic generally refers to electromagnetic waves in the frequency range of 1 kHz to 2000 kHz.

Figure 2:
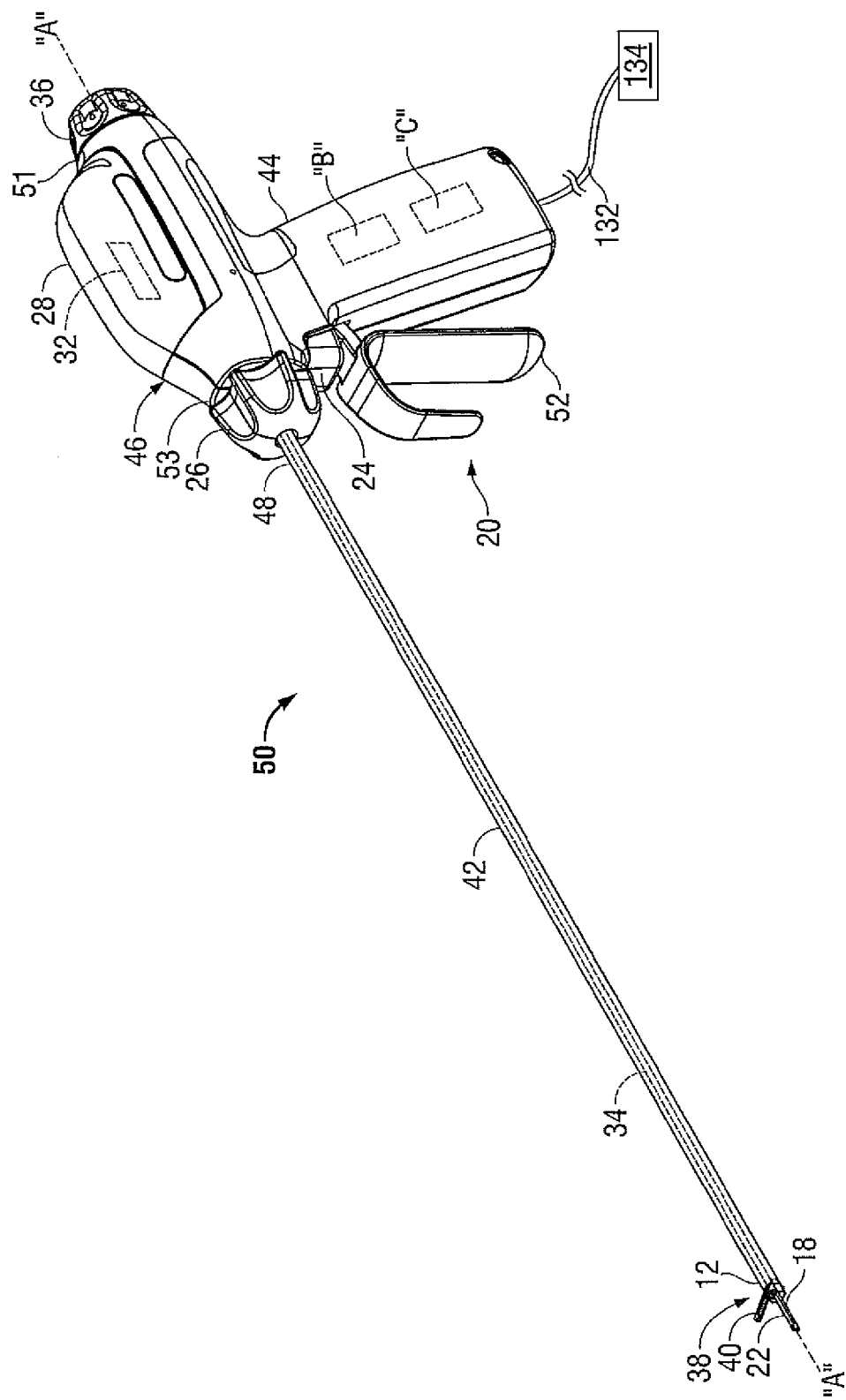
FIG. 2 is a side, perspective view of a handheld surgical instrument according to an embodiment of the present disclosure.
Figure 3:
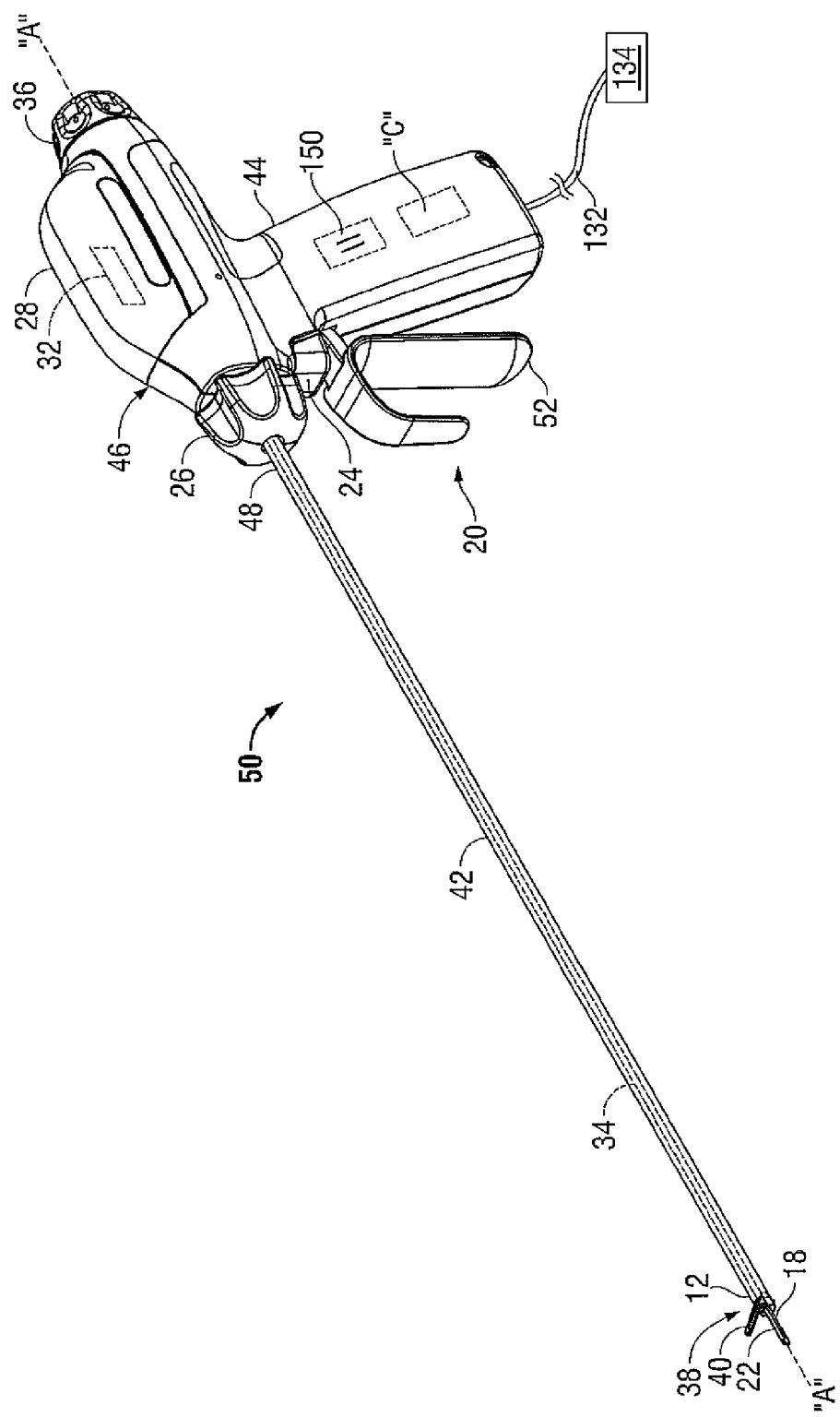
FIG. 3 is a side, perspective view of a handheld surgical instrument according to an alternative embodiment of the present disclosure.

With reference to FIGS. 2-3, and initially with reference to FIG. 2, a handheld surgical instrument 50 configured for use with a removable supplementary DC power supply 134 according to an embodiment of the present disclosure is illustrated. The handheld surgical instrument 50 may be configured for use as, but not limited to, electrosurgical forceps, electrosurgical staplers, etc. For illustrative purposes, FIGS. 2-3 disclose a handheld ultrasonic surgical instrument 50 (instrument 50).

Instrument 50 includes a housing 46 configured to house one or more components, e.g., transducer, waveguide and electrical circuitry that is configured for electrical communication with a battery "B" or a capacitor 150 and the supplementary DC power supply 134 of the instrument 50. A proximal end 51 of housing 46 is configured to couple to an ultrasonic generator 28 (generator 28) and the battery "B" or capacitor 150 (see FIG. 3), described in greater detail below. A distal end 53 of the housing 46 is configured to support and/or couple to a shaft 42.

Shaft 42 extends from housing 46 and defines a longitudinal axis "A-A" therethrough. Shaft 42 includes a length that ranges from about 20 cm to about 40 cm. In the illustrated embodiment, shaft 42 includes a length that is 39 cm. A shaft rotation knob 26 is operably coupled to the shaft 42 and is configured to rotate the shaft 42 approximately 360° in either direction about the longitudinal axis "A-A." A proximal end 48 of the shaft 42 is operably coupled to the housing 46 and a distal end 12 of the shaft 42 is operably coupled to an end effector 38. The operation of parts of the end effector 38 (e.g., jaw members 40 and 18) are movable relative to one another upon actuation of handle assembly 20 coupled to housing 46 as described in more detail below.

More particularly, handle assembly 20 includes a moveable handle 52 and a fixed handle 44. Jaw member 40 is pivotable about jaw member 18 (and/or the distal end 12 of the shaft 42) when lever or movable handle 52 of handle assembly 20 is moved proximally. Jaw member 40 is movable from an open position for positioning tissue between the jaw members 40 and 18, to a clamping position for grasping tissue between the jaw members 40 and 18 and against jaw member 18. Jaw member 18 serves as an active or oscillating blade and is configured to effect tissue. To this end, jaw member 18 includes an ultrasonic member (not shown) that is operably coupled to a transducer 32 (shown in phantom), and an operating surface 22 configured to effect tissue. In the illustrated embodiment, the operating surface 22 is configured to transect, dissect and/or coagulate tissue upon actuation of an activation button 24 operably coupled to generator 28.

Activation button 24 places the instrument 50 in two modes of operation, a low-power mode of operation and a high-power mode of operation. More particularly, activation button 24 is depressable to a first position for delivering low-power to the active jaw member 18 and a second position for delivering high-power to the active jaw member 18. In the first position, one or more audio or visual indicators may indicate to user that the activation button 24 is in the low-power mode. For example, and in one particular embodiment, an audio indicator may include a low-pitch, slow pulsating tone that indicates to a user that the activation button 24 is in the first position or low power mode. Likewise, one or more audio or visual indicators (nor shown) may indicate to user that the activation button is in the high-power mode, e.g., an audio indicator may include a high-pitch, fast pulsating tone that indicates to a user that the activation button 24 is in the second position or high power mode.

Generator 28 is configured to convert electrical energy generated by a battery "B" (FIG. 2) or capacitor 150 (FIG. 3) and supplementary DC power supply 134 to ultrasonic energy to drive the active jaw member 18.

The electrochemistry of battery "B" may be Nickel Cadmium (NiCad), Nickel Metal-Hydride (NiMH), or other type of battery electrochemistry that can withstand high-temperature sterilization cycles. Both NiCad and NiMH batteries can withstand the high temperatures of sterilization with the appropriate temperature buffering in the mechanical design of the housing 46. Additionally, both NiCad and NiMH batteries can withstand least one type of low temperature of sterilization procedure One advantage of using battery "B" is that the instrument 50 is more tolerant to power interruptions or heavy usage because battery "B" maintains a charge longer than capacitor 150.

Capacitor 150 may be used to supplement the power supplied to the end effector 38 during peak requirements. Capacitor 150 may be a conventional capacitor, an ultracapacitor (electric-double layer capacitor), a nanoscale supercapacitor, or other type of known capacitor. Ultracapacitors can release energy faster then a battery and have short re-charging cycles. A nanoscale supercapacitor may be formed from a nanopourous anodic aluminum oxide film followed by an atomic layer deposition of metal, insulator, and metal. Capacitor 150 is configured to withstand high and/or low temperature sterilization procedures.

Generator 28 operably couples to the housing 46 and may be selectively removable therefrom. More specifically and in one embodiment, to secure the generator 28 to the housing 46, a user positions the generator 28 on a top portion of the housing 46 at a proximal end thereof and turns a torquing knob 36 to hand tighten the generator 28 to the housing 46. In certain embodiments, a torque wrench (not shown) may be utilized to control rotation of the torquing knob 36.

Generator 28 also includes transducer 32 (shown in phantom) that is configured to convert electrical energy to mechanical energy that produces motion of a waveguide 34 disposed in operative communication with the active jaw member 18. When the transducer 32 and waveguide 34 are driven at a specific resonant frequency, they produce mechanical motion at the active jaw member 18. The electronics of the generator 28 converts the electrical energy from battery "B" or capacitor 150 and the supplementary DC power supply 134 into a high voltage AC waveform which, in turn, drives the transducer 32. In one particular embodiment, the frequency of this AC waveform is the same as the resonant frequency of the waveguide 34 and transducer 32. As can be appreciated, the magnitude of the AC waveform includes a value that produces the proper amount of mechanical motion.

Handle 44 also includes electrical circuitry (not shown) therein that is utilized to provide communication between the generator 28, the controller "C", and the battery "B" or capacitor 150, and the supplementary DC power supply 134.

The supplementary DC power supply 134 is connected through cable 132 which may be detachable from instrument 50 and or the supplementary DC power supply 134. The supplementary DC power supply 134 may recharge battery "B" or capacitor 150 when the instrument 50 is idle, e.g., when power is not being supplied to active jaw member 18. Additionally, the supplementary DC power supply 134 may selectively augment the power supplied from battery "B" or capacitor 150 to generator 28. Alternatively, the supplementary DC power supply 134 may supply power directly to generator 28.

The supplementary DC power supply 134 may also be detachably coupled to the instrument 50 through cable 132. The supplementary DC power supply may be an AC to DC converter, a DC to DC converter, DC power source, or other similar power supply. The supplementary power supply 134 may be disposed outside the sterile surgical environment, and therefore does not require sterilization. The AC/DC converter may plug into an outlet inside or outside the sterile surgical environment. The DC power source could be a lithium ion battery that is stored outside the sterile surgical environment, and therefore does not need to be sterilized. Cable 132 is sufficiently long enough to allow the user sufficient maneuverability and connect to the supplementary DC power source 134 that may be inside or outside the sterile surgical environment. Additionally, cable 132 can be permanently attached to the handheld surgical instrument 50 (FIGS. 2-3), 100 (FIG. 4-6), or 510 (FIGS. 7A-7C) or completely removable from the handheld instrument 50, 100, or 510 to allow replacement or substitution of a differently sized cable. Cable 132 can be sterilized with the handheld surgical instrument 50, 100, or 510 or separately from the handheld surgical instrument depending on how the cable 132 is connected. For example, cable 132 is removable from the supplementary DC power supply 134 to allow sterilization of cable 132 without the need to sterilize the supplementary DC power supply 134.

Figure 4:
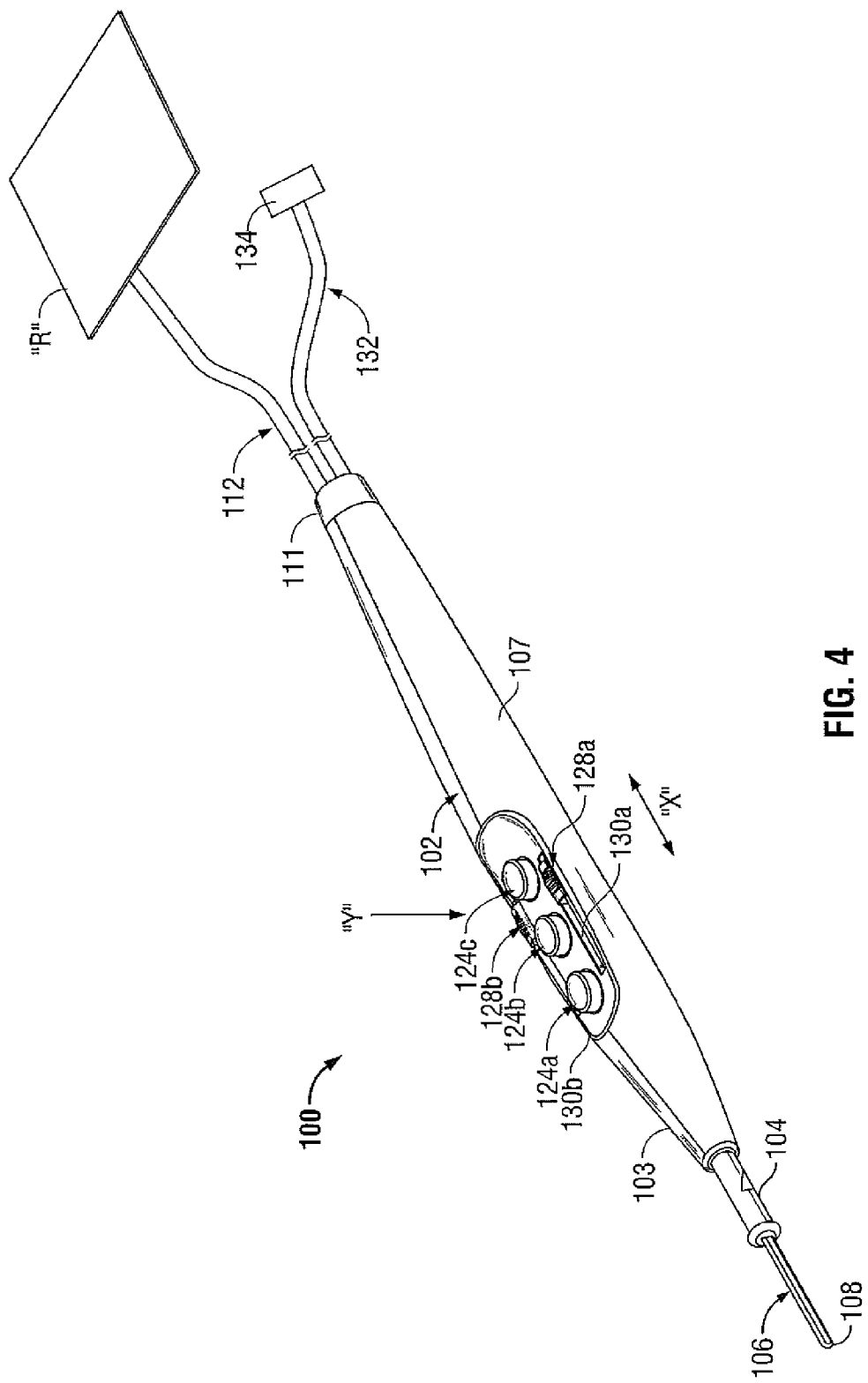
FIG. 4 is a perspective view of an electrosurgical pencil in accordance with an embodiment of the present disclosure.
Figure 5:
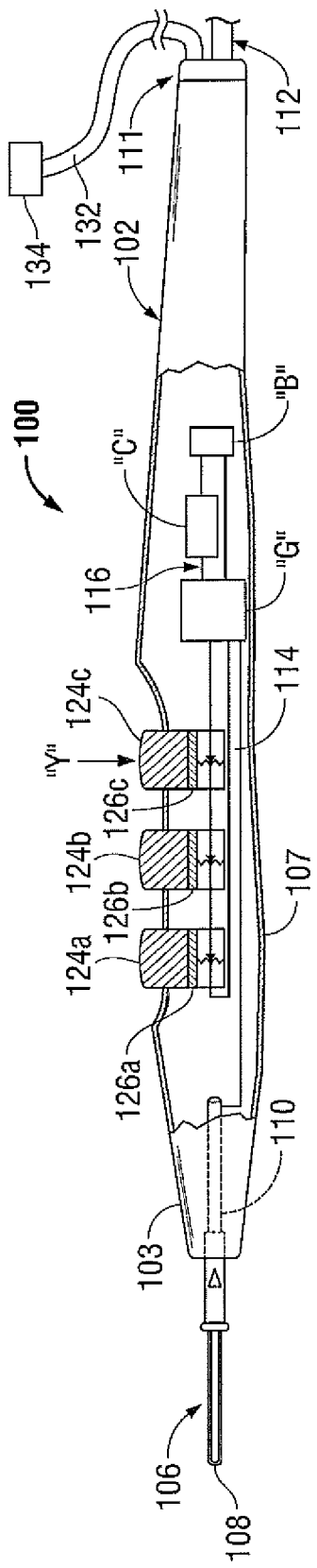
FIG. 5 is a partially broken away, side elevational view of the electrosurgical pencil of FIG. 4.

FIGS. 4-5 show an electrosurgical pencil constructed in accordance with an embodiment of the present disclosure and is shown generally as 100. Electrosurgical pencil 100 includes an elongated housing 102 configured and adapted to support a blade receptacle 104 at a distal end 103 thereof which, in turn, receives a replaceable electrocautery end effector 106 in the form of a loop and/or blade therein. Electrocautery blade 106 is understood to include a planar blade, a loop, a needle and the like. A distal end portion 108 of blade 106 extends distally from receptacle 104 while a proximal end (not shown) portion of blade 106 is retained within distal end 103 of housing 102. Electrocautery blade 106 may be fabricated from a conductive type material, such as, for example, stainless steel, or is coated with an electrically conductive material. The electrosurgical pencil also includes a generator board "G", a controller board "C", and a battery "B" (See FIG. 5).

As shown, electrosurgical pencil 100 is coupled to a return pad "R" via a cable 112. Cable 112 includes a transmission wire that electrically interconnects return pad "R" with a return port 111 defined in electrosurgical pencil 100 to connect the return pad "R" to the generator "G".

For the purposes herein, the terms "switch" or "switches" includes electrical actuators, mechanical actuators, electro-mechanical actuators (rotatable actuators, pivotable actuators, toggle-like actuators, buttons, etc.) or optical actuators.

Electrosurgical pencil 100 includes at least one activation button, e.g., three activation buttons 124a-124c, each of which is supported on an outer surface 107 of housing 102. Each activation button 124a-124c is operatively connected to a respective control switch 126a-126c which, in turn, regulates the transmission of electrical energy supplied from the electrosurgical generator "G" to electrosurgical blade 106. More particularly, control switches 126a-126c are electrically coupled to a control loop 116 and are configured to close and/or complete control loop 116, which causes the controller board "C" to send an instruction to electrosurgical generator "G". Power is then supplied to the generator "G" from battery "B" and/or the supplementary DC power supply 134. The supplementary DC power supply 134 is connected through a cable 132 which may be detachable from the surgical device 100 and or the supplementary DC power supply 134. The supplementary DC power supply 134 recharges battery "B" when the surgical device 100 is idle, e.g., when power is not being supplied to the electrosurgical blade 106. As in FIGS. 2-3, the electrochemistry of battery "B" may be Nickel Cadmium (NiCad), Nickel Metal-Hydride (NiMH), or other type of battery electrochemistry that can withstand high-temperature sterilization cycles with the appropriate temperature buffering in the mechanical design of the housing 102.

Figure 6:
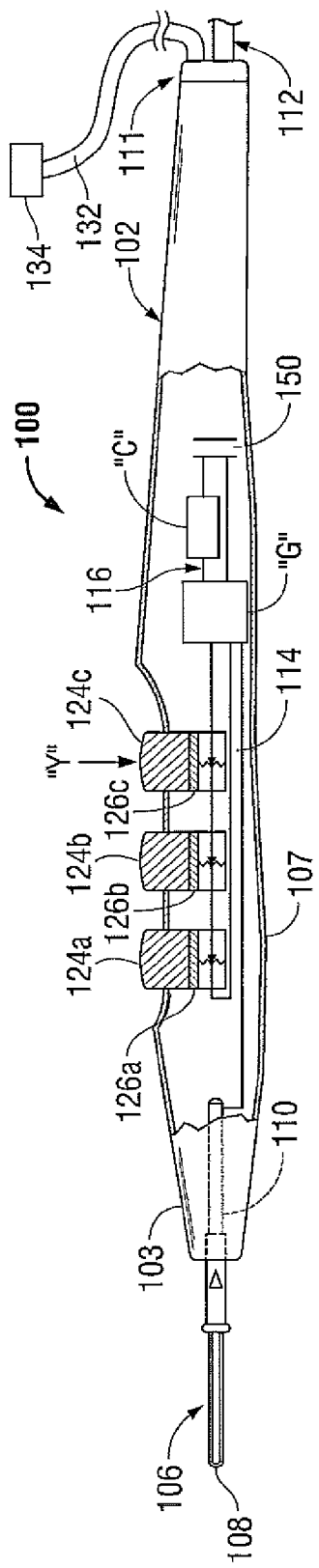
FIG. 6 is a partially broken away, side elevational view of an alternative embodiment of the electrosurgical pencil of FIG. 4.

Alternatively, as shown in FIG. 6, the power is supplied from a capacitor 150 and/or the supplementary DC power supply 134. The supplementary DC power 134 may provide energy for normal continuous operation and/or supply may be used to maintain and/or recharge the capacitor 150. Capacitor 150 may be used to supplement the power supplied to the end effector 106 during peak requirements. As similar to FIG. 3, capacitor 150 may be a conventional capacitor, an ultracapacitor (electric-double layer capacitor), a nanoscale supercapacitor, or other type of known capacitor.

Electrosurgical pencil 100 further includes one or more intensity controllers 128a and/or 128b, each of which are slidingly supported in guide channels 130a, 130b, respectively, defined in outer surface 107 of housing 102. Each intensity controller 128a and 128b is a slide-like potentiometer. Each intensity controller 128a and 128b and respective guide channel 130a and 130b may be provided with a series of cooperating discreet or detented positions defining a series of positions that allow easy selection of output intensity from a minimum amount to a maximum amount. The series of cooperating discreet or detented positions also provides the surgeon with a degree of tactile feedback. One of the series of positions for intensity controllers 128a, 128b may be an "off" position (i.e., no level of electrical or RF energy is being transmitted).

Intensity controllers 128a and 128b are configured and adapted to adjust one of the power parameters (e.g., RF energy field, voltage, power and/or current intensity) and/or the power verses impedance curve shape to affect the perceived output intensity.

As shown in FIGS. 5 and 6, controller board "C" receives inputs from the various switches 126a-126c and intensity controllers 128a-128b that are disposed in housing 102 and sends a signal to the generator "G" to generate an energy signal. The energy signal may be RF, ultrasonic, or other signal selected by the user. The generator is powered from the supplementary DC power supply 134, the battery "B", and/or the capacitor 150.

Figure 7A:
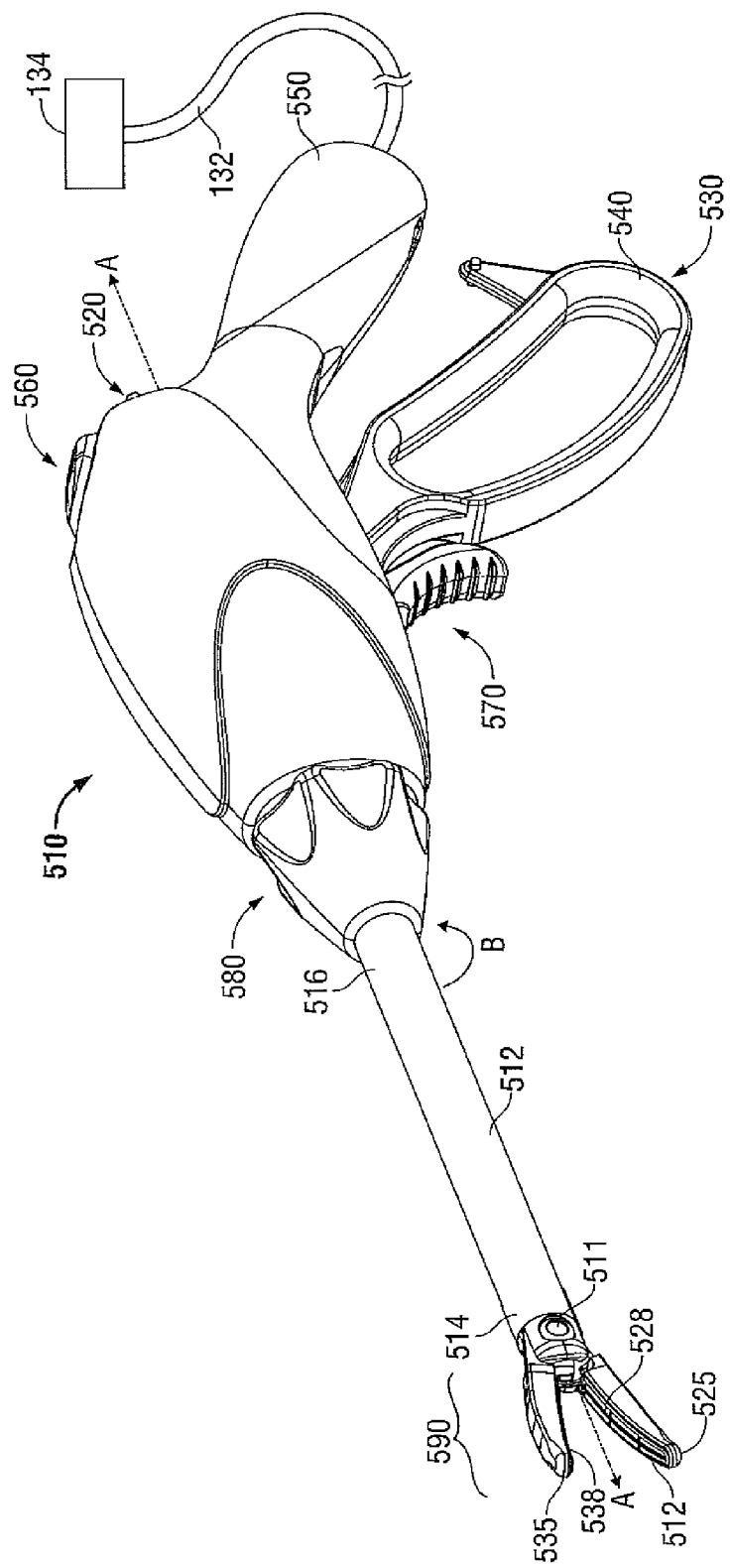
FIG. 7A is a perspective view of an endoscopic forceps and generator according to the present disclosure.
Figure 7B:
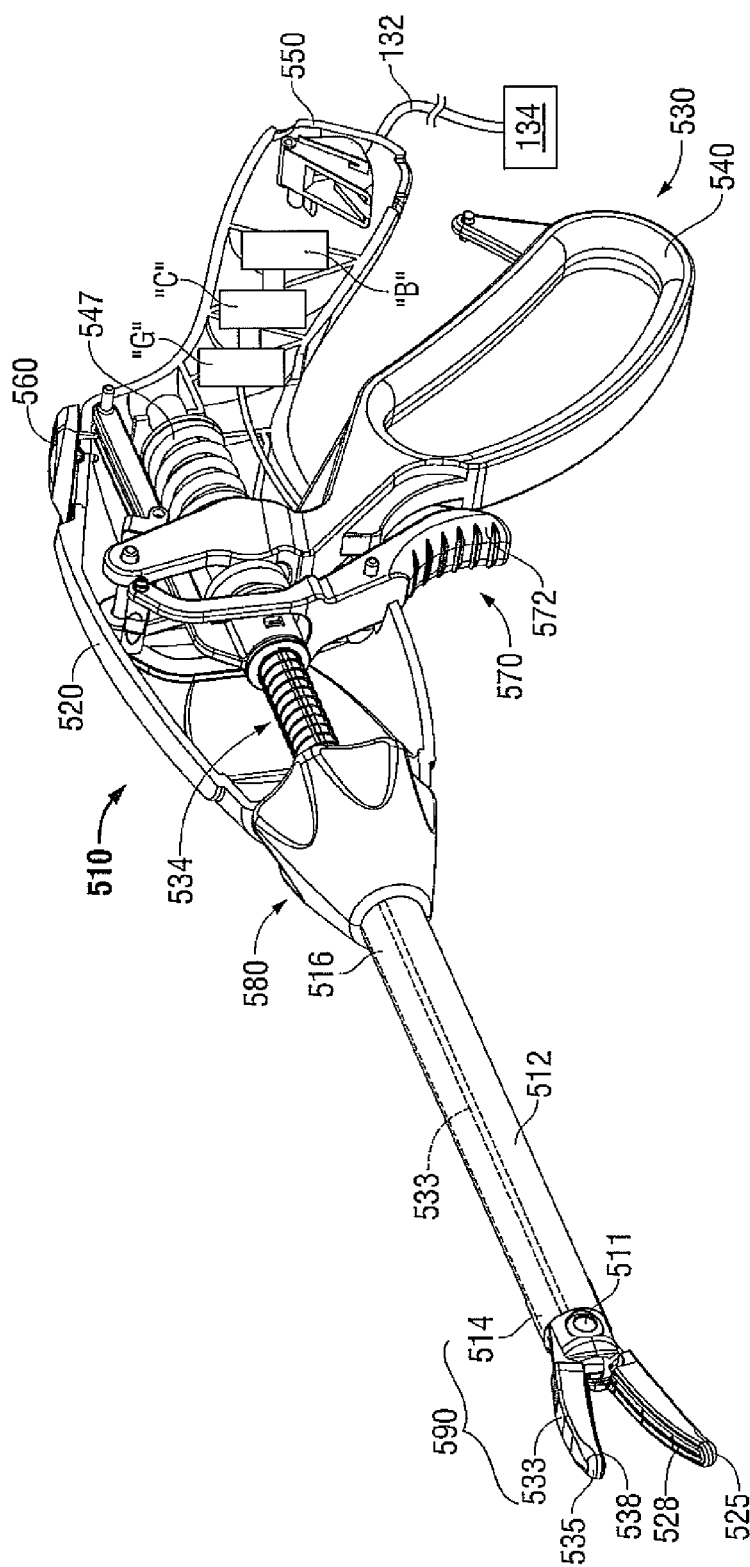
FIG. 7B is interior perspective view of the endoscopic forceps of FIG. 7A according to the present disclosure.

With reference to FIGS. 7A and 7B, an illustrative embodiment of a wireless electrosurgical apparatus, e.g., a bipolar forceps 510 (forceps 510) is shown. Forceps 510 includes an electrosurgical generator "G", a battery "B", and a supplementary DC power supply 134 for performing an electrosurgical procedure (See FIG. 7B). The electrosurgical procedure may include sealing, cutting, cauterizing coagulating, desiccating, and fulgurating tissue all of which may employ RF energy. The electrosurgical generator "G" may be configured for monopolar and/or bipolar modes of operation and may include or be in operative communication with a system (not shown) that may include one or more processors in operative communication with one or more control modules that are executable on the processor. The control module (not explicitly shown) may be configured to instruct one or more modules to transmit electrosurgical energy, which may be in the form of a wave or signal/pulse to the forceps 510.

Forceps 510 is shown configured for use with various electrosurgical procedures and generally includes a housing 520, a rotating assembly 580, a handle assembly 530, and a trigger assembly 570. The trigger assembly 570 includes a finger actuator 572. For a more detailed description of the housing 520, rotating assembly 580, and trigger assembly 570, reference is made to commonly-owned U.S. patent application Ser. No. 11/595,194 filed on Nov. 9, 2006, now U.S. Patent Publication No. 2007/0173814.

With continued reference to FIGS. 7A and 7B, forceps 510 includes a shaft 512 that has a distal end 514 configured to mechanically engage an end effector assembly 590 and a proximal end 516 that mechanically engages the housing 520.

Handle assembly 530 includes a fixed handle 550 and movable handle 540. Fixed handle 550 is integrally associated with housing 520 and handle 540 is movable relative to fixed handle 550 for effecting movement of one or more components, e.g., a drive wire 533 (shown in phantom in FIG. 7B), operably associated with a drive assembly 534 via one or more suitable mechanical interfaces, e.g., a linkage interface, gear interface, or combination thereof.

Drive assembly 534 is in operative communication with handle assembly 530 (see FIGS. 7A and 7B) for imparting movement of one or both jaw members 525, 535 of end effector assembly 590. The drive assembly 534 may include a compression spring 547 that cooperates with drive wire 533 to facilitate closing the jaw members 525 and 535 with uniform and consistent pressure. Drive wire 533 is configured such that proximal movement thereof causes the movable jaw members 535 and 545 and operative components associated therewith, e.g., seal plate 528 and 538, to pivot relative to one another about pivot 511 to approximate tissue. With this purpose in mind, drive rod or wire 533 may be made from any suitable material and is proportioned to translate within the shaft 512. In the illustrated embodiments, drive wire 533 extends through the shaft 512.

Figure 7C:
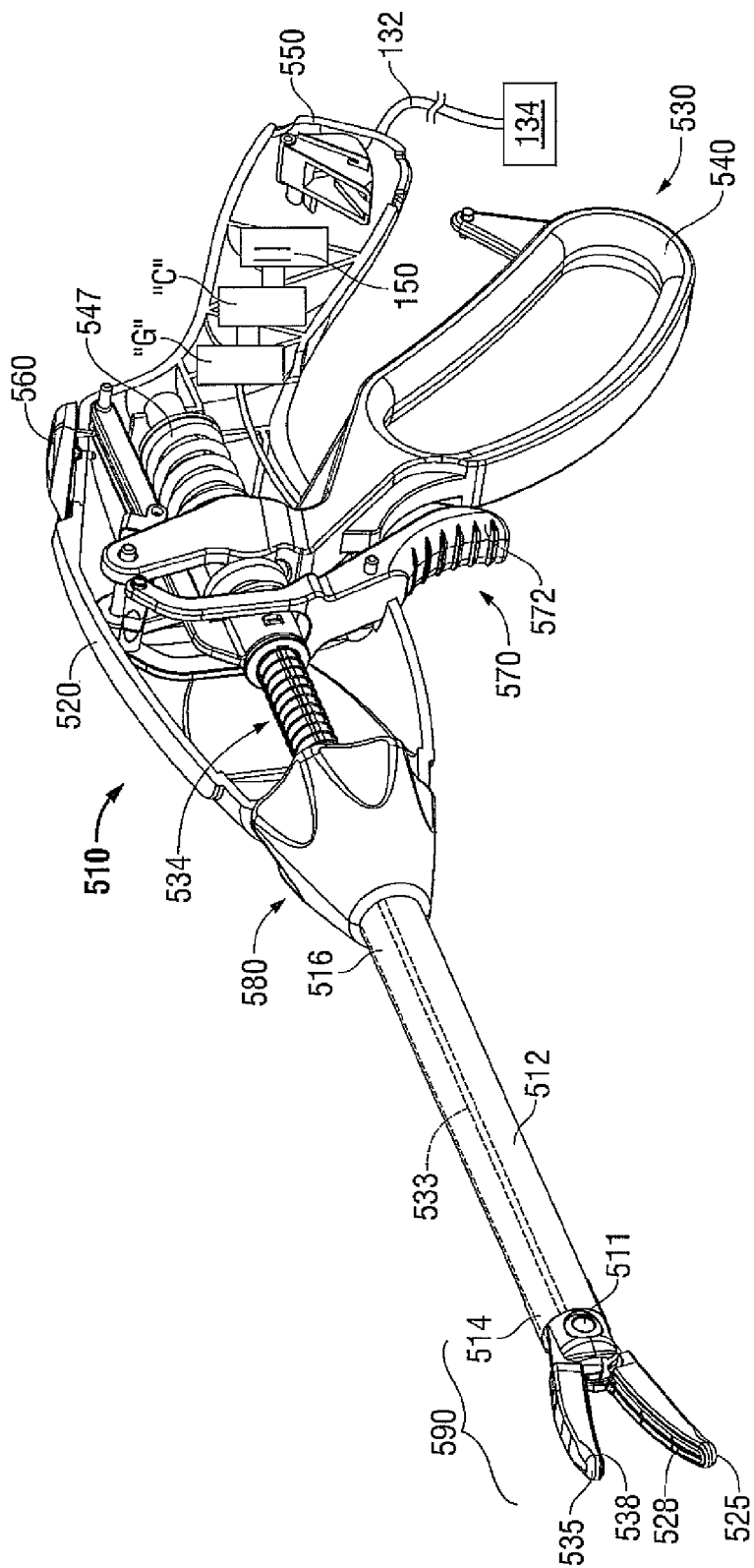
FIG. 7C is interior perspective view of the endoscopic forceps of FIG. 7A according to an alternative embodiment of the present disclosure.

RF energy is supplied from the generator "G" when a user presses switch 560 via controller "C". The power to generate the RF energy signal is supplied from battery "B" and or the supplementary DC power supply 134. The electrochemistry of battery "B" may be Nickel Cadmium (NiCad), Nickel Metal-Hydride (NiMH), or other type of battery electrochemistry that can withstand high-temperature sterilization cycles. Further the supplementary DC supply 134 may be an AC/DC converter, DC/DC converter, a large lithium ion battery, or other similar power supply. The cable 132 connecting the supplemental DC power supply 134 is similar to the one used with the ultrasonic instrument 50, however when used with a RF generator "G", the peak power needs are greater and therefore the cable 132 is larger. Also, the larger cable 132 would need a lower inductance impedance to maintain stable power during transient loading conditions. Alternatively, as shown in FIG. 7C, battery "B" may be replaced with a capacitor 150. Capacitor 150 may be a conventional capacitor, an ultracapacitor (electric-double layer capacitor), a nanoscale supercapacitor, or other type of known capacitor.

Figure 8:
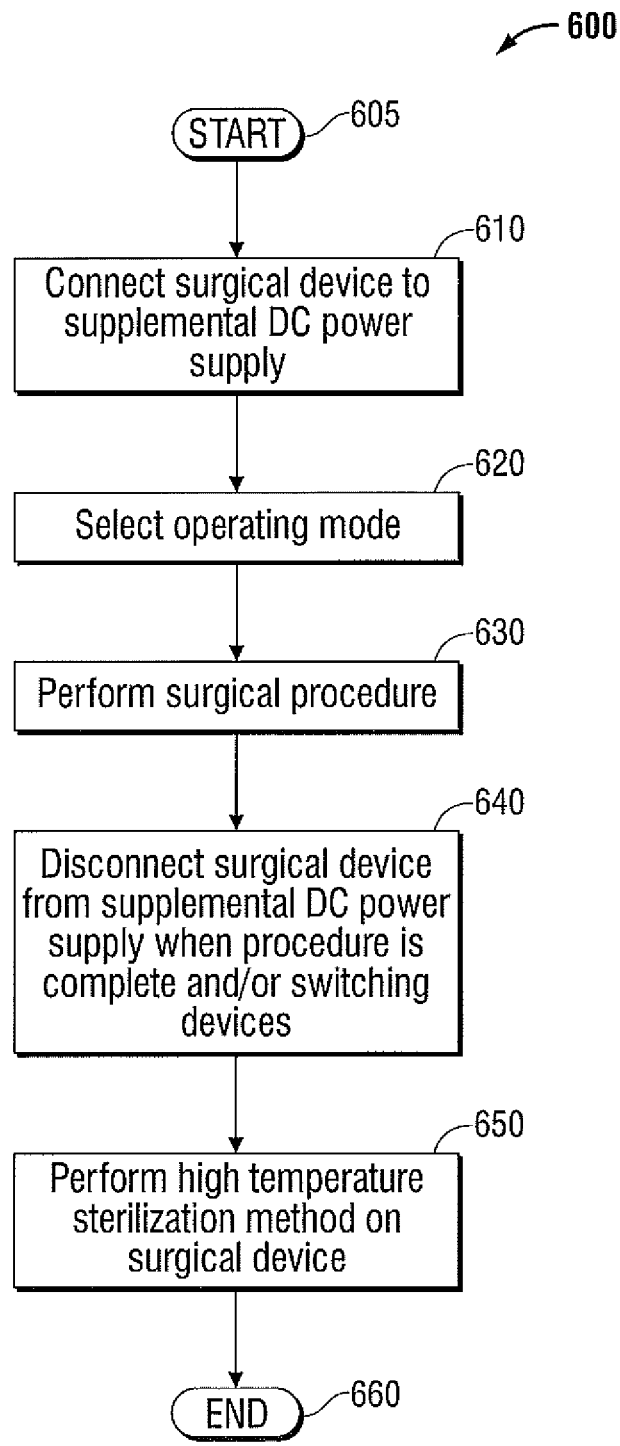
FIG. 8 is a flow chart using a supplementary power supply with a surgical device according to the present disclosure.

FIG. 8 is a flow diagram of process 600 for operating a surgical device, such as instrument 50, 100 or 510, using a supplementary DC power supply 134. The process 600 starts at step 605, and with an operator connecting a surgical instrument 50, 100, or 510 to the supplemental DC power supply 134 at step 610. Next at step 620, an operator selects an operating mode by pressing an activation button or switch, such as 52, 124a-124c or 560, on the handheld device 50, 100, or 510 respectively. The surgeon then performs the surgical procedure at step 630, which can include applying electrical energy at different rates and for different lengths of time. It also may include the use of one or more instruments that may or may not be powered. If multiple powered instruments are used, the user can use multiple supplemental DC power supplies 134 or disconnect cable 132 from the instrument 50, 100, or 510, and connect the new instrument. After the surgical procedure is complete, the user disconnects the supplemental DC power supply 134 from cable 132 at step 640. Cable 132 can be disconnected from the instrument 50, 100, or 510 to be sterilized at step 650. The process 600 ends at step 660 after the instrument 50, 100, or 510 and or cable 132 is sterilized using a high temperature sterilization method at step 650.

The supplementary DC power supply 134 is used to selectively augment the internal power supply, which may be battery "B" or capacitor 150. The power is then supplied to generator 28 or "G". During periods when instrument 50, 100, or 510 is idle, the supplementary DC power supply may recharge battery "B" or capacitor 150. Alternatively, the supplementary DC power supply 134 may supply power directly to generator 28 or "G". Additionally, the internal power supply, which may be battery "B" or capacitor 150, can withstand at least one type of high temperature sterilization while within the instrument. This allows for reduced costs of sterilization because lithium-ion batteries have low heat tolerance and require a hydrogen-peroxide system for sterilization which is more expensive then high temperature sterilization methods.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A handheld ultrasonic surgical device, comprising:
a housing defining a top portion, a proximal portion, and a distal portion;
a waveguide extending distally from the distal portion of the housing and defining a longitudinal axis, the waveguide having a blade and a moveable jaw member disposed at a distal end thereof, the moveable jaw member pivotable with respect to the blade;
a torque knob disposed at the proximal portion of the housing and rotatable about the longitudinal axis defined by the waveguide;
a removable ultrasonic generator couplable to the top portion of the housing at the proximal portion thereof, rotation of the torque knob selectively locking and unlocking the removable ultrasonic generator to the housing;
a transducer couplable to the removable ultrasonic generator and configured to convert electrical energy to mechanical energy, wherein mechanical energy is transmittable through the waveguide to the blade which causes the blade to oscillate and deliver energy to tissue;
a removable battery couplable to the housing and configured to supply electrical energy to the removable ultrasonic generator; and
a AC/DC converter couplable to the housing and configured to supply supplemental energy to the removable ultrasonic generator and selectively recharge the removable battery, wherein the AC/DC converter selectively augments the power supplied to the removable ultrasonic generator, such that if the power supplied by the removable battery is insufficient the AC/DC converter directly powers the removable ultrasonic generator.

2. The handheld ultrasonic surgical device of claim 1, wherein the removable battery is coupled at the proximal portion of the housing.

3. The handheld ultrasonic surgical device of claim 1, wherein the housing includes a moveable handle and a fixed handle, such that articulation of the moveable handle with respect to the fixed handle articulates the moveable jaw member with respect to the blade.

4. The handheld ultrasonic surgical device of claim 1, wherein the housing and the removable battery are constructed of materials to withstand at least one type of high-temperature sterilization.

5. The handheld ultrasonic surgical device of claim 1, wherein the AC/DC converter includes a cord coupled between the AC/DC converter and the housing, further wherein the AC/DC converter is in external communication with at least one of the removable battery and the removable ultrasonic generator.

6. The handheld ultrasonic surgical device of claim 5, wherein the cord is selectively removable from the AC/DC converter to allow the cord to be independently sterilized using at least one type of high-temperature sterilization.

7. The handheld ultrasonic surgical device of claim 1, wherein the AC/DC converter is couplable to the housing at a position thereon such that during use the AC/DC converter is located outside of a sterilized surgical area.

8. The handheld ultrasonic surgical device of claim 1, wherein the AC/DC converter is configured to augment power supplied to the removable ultrasonic generator.

9. The handheld ultrasonic surgical device of claim 1, wherein the AC/DC converter is in selective communication with both the removable ultrasonic generator and the removable battery.

10. The handheld ultrasonic surgical device of claim 1, wherein the AC/DC converter selectively recharges the removable battery when power is not being provided to the removable ultrasonic generator.

11. The handheld ultrasonic surgical device of claim 1, further comprising a controller, the controller configured to receive an instruction from a mechanical actuator relative to an operating mode and send the appropriate instruction to the removable ultrasonic generator to generate a corresponding energy signal.

12. The handheld ultrasonic surgical device of claim 11, wherein the controller is disposed in the housing.

13. The handheld ultrasonic surgical device of claim 11, wherein the controller is configured to control an intensity of the energy signal, the controller configured to adjust at least one of the voltage, power, or current.

14. The handheld ultrasonic surgical device of claim 13, wherein the controller is configured to control the intensity of the energy signal by selectively supplying energy from at least one of the removable battery and the AC/DC converter to the removable ultrasonic generator.

15. The handheld ultrasonic surgical device of claim 11, wherein the mechanical actuator selectively controls the operating mode of the removable ultrasonic generator between a low-power mode and a high-power mode.

16. The handheld ultrasonic surgical device of claim 15, further comprising an indicator indicative of the low-power mode or the high-power mode of the removable ultrasonic generator.

17. The handheld ultrasonic surgical device of claim 16, wherein the indicator is at least one of an audio indicator or a visual indicator.

* * * * *